United States Patent [19]

Malz, Jr. et al.

[11] 4,045,484

[45] Aug. 30, 1977

[54] PROCESS FOR PREPARING N'-METHYL ACETHYDRAZIDE

[75] Inventors: Russell E. Malz, Jr., Naugatuck; Roger W. Amidon, Oxford; Harold Greenfield, Watertown, all of Conn.

[73] Assignee: Uniroyal, Inc., New York, N.Y.

[21] Appl. No.: 698,452

[22] Filed: June 21, 1976

Related U.S. Application Data

[63] Continuation-in-part of Ser. No. 596,544, July 16, 1975, Pat. No. 3,965,174.

[51] Int. Cl.$^2$ .................................... C07C 103/32
[52] U.S. Cl. .................... 260/561 H; 260/583 B
[58] Field of Search ................. 260/561 H, 583 B

[56] References Cited

U.S. PATENT DOCUMENTS

| 3,272,839 | 9/1966 | Bollag et al. | 260/583 B |
| 3,829,492 | 8/1974 | Miller et al. | 260/561 H |

FOREIGN PATENT DOCUMENTS

| 647,481 | 8/1962 | Canada |
| 307,629 | 6/1955 | Switzerland |
| 309,770 | 9/1955 | Switzerland |

*Primary Examiner*—Arthur P. Demers
*Attorney, Agent, or Firm*—Stephen P. Gilbert

[57] ABSTRACT

A process for preparing N'-methylacethydrazide by reacting acethydrazide, a formaldehyde source, and hydrogen in the presence of a palladium catalyst is disclosed.

6 Claims, No Drawings

PROCESS FOR PREPARING N'-METHYL ACETHYDRAZIDE

This application is a continuation-in-part of a previous application, Ser. No. 596,544, now U.S. Pat. No. 3,965,174 filed on July 16, 1975.

N'-methylacethydrazide has substantial utility as an intermediate in the manufacture of methylhydrazine which, in turn, has utility as a rocket fuel ingredient.

Previous methods for the preparation of N'-methylacethydrazide, such as the acylation of methylhydrazine with ethyl acetate or acetic anhydride (Condon, J. Organic Chemistry, Vol. 37, p. 3608, 1972), start with methylhydrazine, which is both difficult to produce and expensive. In addition, this method gives poor yields and the product is contaminated with N-methylacethydrazide and diacetylmethylhydrazines which are difficult to separate from the N'-methylacethydrazide.

Another method of preparation is the methylation of acethydrazide, but this produces a mixture of N'-methyl, N-methyl, N,N'-dimethyl, and N,N',N'-trimethylacethydrazides, which are also difficult to separate.

Methods of producing biologically active, complex hydrazides by reductive alkylation are disclosed in Yale et al., Chemotherapy of Experimental Tuberculosis, Journal of the American Chemical Society, 75, 1933-1941 (1953), Gutmann et al., U.S. Pat. No. 2,970,159, Jan. 31, 1961, and Fox et al., Journal of Organic Chemistry, 18, 944 (1953). Yale et al. and Fox et al. teach the use of platinum catalysts. Gutmann et al. illustrate the use of a ketone and an aromatic aldehyde with platinum in an inert solvent, and in passing, mention the use of platinum and palladium-on-carbon with all carbonyl compounds.

These methods for producing expensive, biologically active, complex hydrazides, however, are not entirely suitable for production of N'-methylacethydrazide.

Thus, it is an object of this invention to provide a process which can be used on a commercial-scale to produce N'-methylacethydrazide economically.

Most unexpectedly it has been discovered that N'-methylacethydrazide can be produced in substantial yields at an economic rate by reacting acethydrazide, a formaldehyde source, and hydrogen in the presence of a palladium catalyst in a solvent medium.

This reaction is represented as follows:

Acethydrazide may be prepared by methods well-known in the art [for example, Lindegren et al., Journal of the American Chemical Society, 71, 1504 (1949)]. The formaldehyde source used may be formaldehyde, paraformaldehyde, or trioxane, or mixtures thereof. Preferably the formaldehyde source is formaldehyde or paraformaldehyde, of which paraformaldehyde is most preferred.

The palladium catalyst may be palladium or palladium oxide or any other salts or complexes of palladium which are converted in situ to palladium and whose non-palladium moieties in no way hinder the reaction. The catalyst may be either unsupported or supported on a carrier such as carbon, alumina, silica, silica alumina, alkaline earth carbonates, kieselguhr, zeolites, pumice, clay, cellulose, asbestos, etc. The catalyst may be used in powdered form for slurry reactions, or in extrudates, pellets, spheres, or granules for fixed bed reactions. The catalyst concentration for batch type reactions is from 0.001 to 50 parts, usually from 0.05 to 10 parts, and most preferably from 0.10 to 5 parts of catalyst per 100 parts of acethydrazide, all parts being by weight.

The solvent of this invention must be water or lower (one to six carbon atoms) aliphatic alcohols or mixtures thereof. Preferred are water, methanol, ethanol, isopropanol, and mixtures thereof. Most preferred are water, methanol, and mixtures thereof. The ratio of solvent to total non-gaseous reactants (the acethydrazide plus the formaldehyde source) is from 0.2/1 to 50/1, usually from 0.3/1 to 5/1, and most preferably from 0.5/1 to 2/1, in units of milliliters/gram.

The molar ratio of acethydrazide to formaldehyde source is from 10/1 to 0.1/1, preferably between 3/1 and 0.33/1, and most preferably from 1.2/1 to 0.8/1.

The gas phase fed to the reactor may be pure hydrogen or a mixture containing hydrogen. The hydrogen partial pressure required for performing this process ranges from 1 to as high as 10,000 psi, but usually is limited to from 10 to 5,000 psi, with partial pressures ranging from 100 to 2,500 psi being most preferred.

The process may be conducted over a temperature range of from 20° to 150° C, and most preferably from about 50° to 120° C.

The reaction may be carried out in batch-type, semi-continuous-flow or continuous-flow equipment.

When employing batch-type processing, a liquid phase containing acethydrazide, formaldehyde source, palladium catalyst, and solvent are charged to the reactor, after which the reaction vessel is purged with an inert gas such as nitrogen or helium, and then with hydrogen. Thereafter, optionally while agitating the reaction mixture, the reactor is pressurized with hydrogen to the desired pressure, agitation is started or continued, and heat is added or removed, as necessary, to achieve the desired reaction temperature. During the reaction period, which may be from 10 minutes to 48 hours for batch-type reactors, additional hydrogen is added to compensate for that consumed by the reaction. (It shall be apparent to one skilled in the art that the residence or contact time may vary greatly depending on the conversion desired and the reaction system employed, e.g., in a continuous, fixed-bed type process, the residence time may range from 1 second to 30 minutes).

At the end of the reaction period excess hydrogen is vented. The reactor contents are then filtered in order to separate the catalyst, an standard techniques such as distillation or crystallization may be used to recover the crude product from the catalyst-free mixture. A pure product may be recovered from the crude product by known recrystallization methods. Optionally, after releasing the excess hydrogen and without further purification, the reactor contents may be used directly for the production of methylhydrazine.

steel Magne Drive autoclave with 44.4 g (0.60 mole) of acethydrazide, 20.4 g (0.66 equiv) of 97% paraformaldehyde, 60 ml of solvent, and a specified amount of 5% palladium carbon catalyst. The reaction products were treated and analyzed as in Example 1. Results are summarized in the Table below.

TABLE
EXAMPLE 2

| Expt. No. | Temp., ° C | Pressure, psig | Catalyst wt., g | Solvent | Time, hr (a) | Time, hr (b) | % Recovery acethydrazide | % Yield N'-methyl-acethydrazide | % Yield N,N'-dimethyl-acethydrazide |
|---|---|---|---|---|---|---|---|---|---|
| A | 70 | 400–600 | 0.10 | water | 5.0 | 4.3 | 3 | 67 | 20 |
| B | 70 | 400–600 | 0.10 | methanol | 6.4 | 5.8 | <1 | 68 | 19 |
| C | 100 | 100–200 | 0.15 | water | 5.6 | 5.6 | 3 | 5 | 18 |
| D | 100 | 100–200 | 0.15 | methanol | 5.6 | 5.0 | 18 | 38 | 36 |
| E | 100 | 400–600 | 0.05 | water | 5.0 | 5.0 | 15 | 19 | 33 |
| F | 100 | 400–600 | 0.05 | methanol | 5.0 | 4.0 | 9 | 42 | 29 |
| G | 100 | 400–600 | 0.125 | water | 4.7 | 4.2 | 17 | 35 | 34 |
| H | 100 | 400–600 | 0.125 | methanol | 1.5 | 0.7 | 5 | 64 | 23 |
| I | 100 | 900–1200 | 0.025 | water | 3.3 | 3.3 | 17 | 28 | 31 |
| J | 100 | 900–1200 | 0.025 | methanol | 3.3 | 2.7 | 8 | 46 | 28 |
| K | 130–5 | 400–600 | 0.05 | water | 8.7 | 8.7 | 18 | 19 | 19 |
| L | 130–5 | 400–600 | 0.05 | methanol | 1.5 | 0.8 | 16 | 37 | 19 |

(a) Time at specified temperature
(b) Time at specified temperature during hydrogen absorption It shall be appreciated by one skilled in the art that the various reaction parameters (formaldehyde source, solvent, concentrations of reactants and catalyst, temperature, hydrogen partial pressure, residence or contact time, flow-scheme, conversions of formaldehyde source and acethydrazide per pass, etc.) are interrelated and may be chosen within the ranges set forth above so as to optimize the entire production scheme.

The following examples illustrate the advantages of and the practice of this invention.

EXAMPLE 1A

A mixture of 29.6 g (0.40 mole) of acethydrazide, 12.4 g (0.40 equiv) of 97% paraformaldehyde, 83 ml of water, and 0.20 g of 5% palladium on carbon was added to a 600-ml stainless-steel Magne Drive autoclave. The vessel was sealed, purged first with nitrogen and then with hydrogen, and pressured with hydrogen to 500 psig. The autoclave was heated with agitation for 2.7 hr at 70°–75° C and 400–600 psig with little or no gas absorption in the last 0.2 hr. The autoclave was cooled and depressurized. The reaction mixture was filtered through diatomaceous earth to separate the catalyst. The solvent was removed in a rotary evaporator on a steam bath at reduced pressure in a nitrogen atmosphere, using codistillation with benzene at the end of the process for water removal. The liquid residue was analyzed by quantitative glpc analysis. It was found to contain ca. 0.2 g (< 1% recovery) of unreacted acethydrazide, 29.4 g (83% yield) of N'-methylacethydrazide, and 4.2 g (10% yield) of N',N'-dimethylacethydrazide.

EXAMPLE 1B

Example 1A was repeated with methanol as the solvent for 2.7 hr at 70°–75° C and 400–600 psig, and gave ca. 0.3 g (< 1% recovery) of unreacted acethydrazide, 26.1 g (74% yield of N'-methylacethydrazide, and 3.3 g (8% yield) of N',N'-dimethylacethydrazide.

EXAMPLE 2

The procedure of Examples 1A and 1B was repeated at various temperatures, times, and catalyst concentrations. Each experiment was run in a 600-ml stainless-

EXAMPLE 3

Example 2F was repeated with isopropanol as the solvent for 5.2 hr at 100° C and 400–600 psig, and gave 6.5 g (15% recovery) of unreacted acethydrazide, 18.8 g (36% yield) of N'-methylacethydrazide, and 18.6 g (30% yield) of N',N'-dimethylacethydrazide.

EXAMPLE 4

A mixture of 44.4 g (0.60 mole) of acethydrazide, 52.1 g (0.66 equiv) of 38% aqueous formaldehyde solution containing 10–15% methanol, 33 ml of water, and 2.5 g of 5% palladium on carbon was added to a 600-ml stainless-steel Magne Drive autoclave. The vessel was sealed, purged first with nitrogen and then with hydrogen and pressured with hydrogen to 500 psig. The autoclave was heated with agitation at 45°–50° C and 400–600 psig for 3.0 hr. The autoclave was cooled and depressurized. The reaction mixture was filtered through diatomaceous earth to separate the catalyst. The solvent was removed in a rotary evaporator on a steam bath at reduced pressure in a nitrogen atmosphere, using codistillation with benzene at the end of the process for water removal. The liquid residue was analyzed by quantitative glpc analysis. It was found to contain 2.4 g (5.5% recovery) of unreacted acethydrazide, 11.9 g (23% yield) of N'-methylacethydrazide, and 14.6 g (24% yield) of N',N'-dimethylacethydrazide.

We claim:

1. A process for the production of N'-methylacethydrazide which comprises reacting acethydrazide, paraformaldehyde, and hydrogen, in a solvent and in the presence of a palladium catalyst, said solvent being selected from the group consisting of water, lower aliphatic alcohols, and mixtures thereof, at a temperature of from 20° to 150° C, a hydrogen partial pressure of from 1.0 to 10,000 psi, and an equivalent ratio of acethydrazide to paraformaldehyde of from 0.1/1 to 10/1.

2. The process of claim 1 wherein the solvent is selected from the group consisting of water, methanol, ethanol, isopropanol, and mixtures thereof.

3. The process of claim 1 wherein the temperature is from 50° to 120° C.

4. The process of claim 1 wherein the palladium catalyst is selected from the group consisting of palladium and palladium oxide.

5. A process for the production of N'-methylacethydrazide which comprises reacting acethydrazide, paraformaldehyde, and hydrogen in a solvent chosen from the group consisting of water, methanol, isopropanol, and mixtures thereof, in the presence of a palladium catalyst, at a temperature of from 50° to 120° C and a hydrogen partial pressure of 10 to 5,000 psi, wherein the molar ratio of acethydrazide to paraformaldehyde is from 0.33/1 to 3/1, and wherein the palladium catalyst is selected from the group consisting of palladium and palladium oxide.

6. The process of claim 5 wherein the solvent is selected from the group consisting of water, methanol, and mixtures thereof, the hydrogen partial pressure is 100 to 2,500 psi, and the molar ratio of acethydrazide to paraformaldehyde is from 0.8/1 to 1.2/1.

* * * * *